United States Patent [19]
Wang

[11] Patent Number: 5,645,749
[45] Date of Patent: Jul. 8, 1997

[54] HEAT PACK CAPABLE OF BEING RECHARGED BY MICROWAVE ENERGY

[76] Inventor: Charles Wang, 6F-3, No. 213, Fu-Ho Road,, Yung-Ho City, Taipei, Taiwan

[21] Appl. No.: 511,219

[22] Filed: Aug. 4, 1995

[51] Int. Cl.$^6$ .................... H05B 6/80; F24J 1/00
[52] U.S. Cl. ............ 219/759; 219/736; 219/745; 126/263.01; 126/263.07; 126/263.09; 607/101
[58] Field of Search .................... 219/759, 730, 219/736, 745; 99/DIG. 14; 126/263.01, 263.03, 263.04, 263.06, 263.07, 263.08, 263.09, 204; 607/96, 101, 108, 109, 110, 112

[56] References Cited

U.S. PATENT DOCUMENTS

| | | |
|---|---|---|
| 4,077,390 | 3/1978 | Stanley . |
| 4,572,158 | 2/1986 | Fiedler . |
| 4,656,069 | 4/1987 | Traut ........................ 343/872 |
| 4,743,728 | 5/1988 | Hughes et al. ............. 219/759 |
| 4,829,980 | 5/1989 | Smith ...................... 126/263.09 |
| 4,880,953 | 11/1989 | Manker . |
| 4,899,727 | 2/1990 | Kapralis et al. .......... 126/263.04 |
| 4,914,717 | 4/1990 | Gibbon ..................... 219/759 |
| 5,056,589 | 10/1991 | Hettel et al. .............. 126/263.08 |
| 5,070,223 | 12/1991 | Colasante .................. 219/759 |
| 5,205,278 | 4/1993 | Wang ....................... 126/263.03 |
| 5,275,156 | 1/1994 | Milligan et al. ........... 607/114 |
| 5,305,733 | 4/1994 | Walters ..................... 126/263.01 |

*Primary Examiner*—Philip H. Leung
*Attorney, Agent, or Firm*—Bacon & Thomas

[57] ABSTRACT

A heat pack including a flexible water-tight plastic bag, saturated sodium acetate solution contained in the plastic bag, and an activator disposed in contact with the saturated sodium acetate solution and operated to activate the saturated sodium acetate solution, causing the saturated sodium acetate solution to crystallize, wherein the activator is covered within a plastic shell. According to another embodiment of the invention, the activator is a metal plate having a frosted outside wall.

1 Claim, 4 Drawing Sheets

HEAT PACK CAPABLE OF BEING RECHARGED BY MICROWAVE ENERGY

BACKGROUND OF THE INVENTION

The present invention relates to heat packs, and relates more particularly to such a heat pack which is capable of being recharged by microwave energy.

Heat packs which utilize saturated sodium acetate solution that can be activated to liberate heat have become increasingly popular in recent years. Exemplar of these heat packs can be seen in U.S. Pat. No. 4,077,390. U.S. Pat. No. 4,880,953 teaches a method of recharging or regenerating a substantially solid spent heat pack of the type in which a super-coolable salt solution is confined within a flexible plastic pouch and converted to solid form with evolution of heat, by contacting the solid contents of the pack with a source of microwave energy sufficient to melt the solid to the liquid state, without thereby damaging the heat pack. However, the heat pack used in U.S. Pat. No. 4,880,953 does not allow internal welds to be made between the two opposite side walls of the flexible plastic pouch. Furthermore, because the activator is a metallic means, it tends to reflect microwave energy onto a limited area to regenerate the spent heat pack.

SUMMARY OF THE INVENTION

It is one object of the present invention to provide a heat pack that can be regenerated by microwave energy, and in which the flexible plastic bag has internal welds between the two opposite side walls. It is another object of the present invention to provide a heat pack that eliminates the problem of reflecting microwave energy onto a limited area. According to the present invention, the heat pack comprises a flexible water-tight plastic bag, saturated sodium acetate solution contained in the plastic bag, and an activator disposed in contact with the saturated sodium acetate solution and operated to activate the saturated sodium acetate solution, causing the saturated sodium acetate solution to crystallize an exothermic reaction ensues. The activator can be metal springs covered within a plastic shell, or a metal plate having a frosted outside surface. The plastic shell or frosted outside surface does not reflect microwave, therefore the problem of reflecting microwave energy onto a limited area is eliminated.

DETAILED DESCRIPTION OF THE PREFERRED EMBODIMENT

Figure 1:
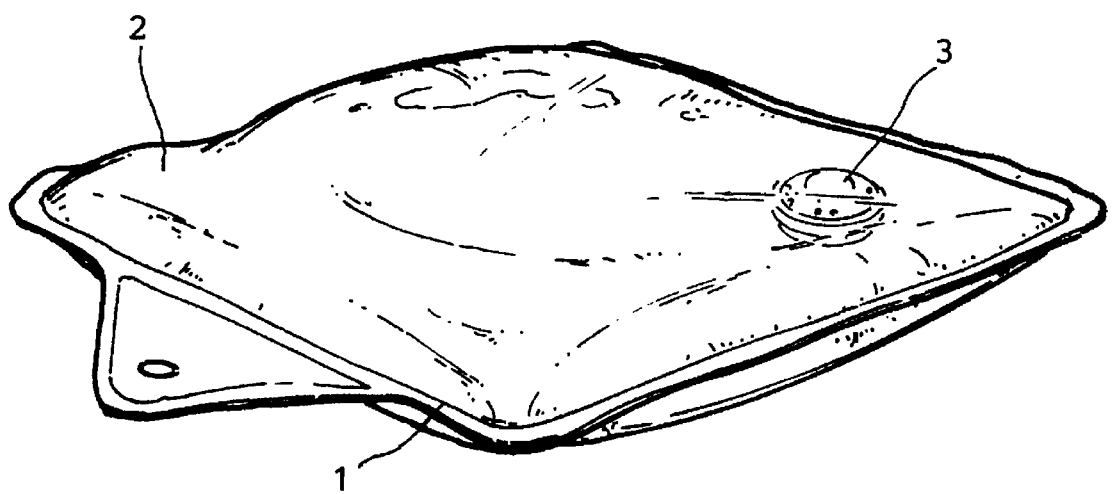
FIG. 1 shows a heat pack according to the present invention.

Referring to FIG. 1, the heat pack in accordance with the preferred embodiment of the present invention is generally comprised of a flexible water-tight plastic bag 1, saturated sodium acetate solution 2 contained in the plastic bag 1, and an activator 3 disposed in contact with saturated sodium acetate solution 2 for activating saturated sodium acetate solution 2, causing it to pass from the liquid phase to a crystalline substantially solid phase with the generation of heat.

Figure 2:
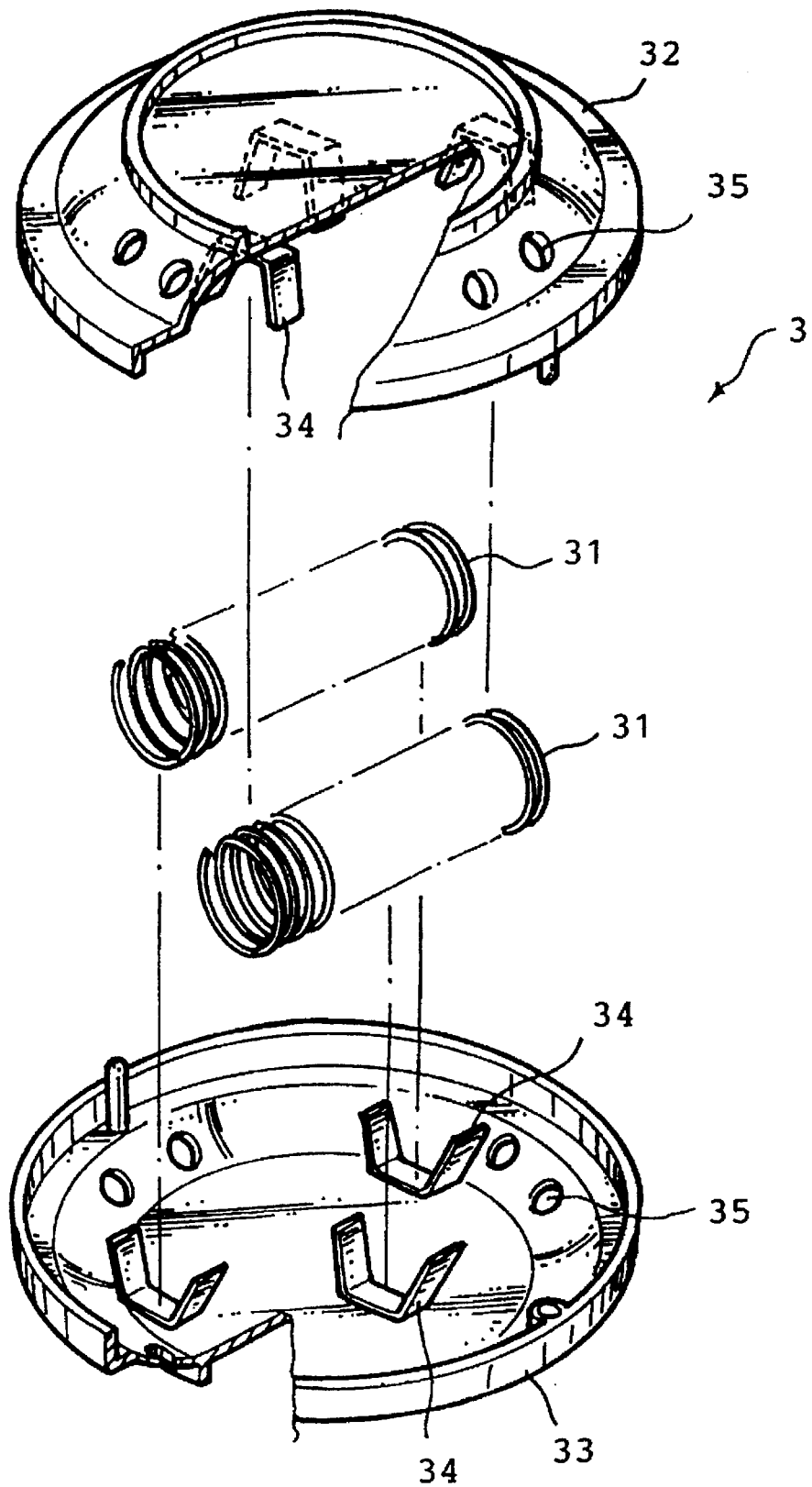
FIG. 2 is an exploded view of the activator for the heat pack showing in FIG. 1.

Referring to FIG. 2, the activator 3 comprises a plastic casing 33, a pair of metal springs 31 mounted in the plastic casing 33, and a plastic cover 32 covered on the plastic casing 33 over the metal springs 31. The plastic cover 32 and the plastic casing 33 have two sets of spring holders 34 for mounting the metal springs 31. The plastic casing 33 and the plastic cover 32 are compressible. A plurality of through holes 35 are respectively made on the plastic casing 33 and the plastic cover 32. Through the through holes 35, saturated sodium acetate solution 2 enters the activator 3 into contact with the metal springs 31.

Figure 3:
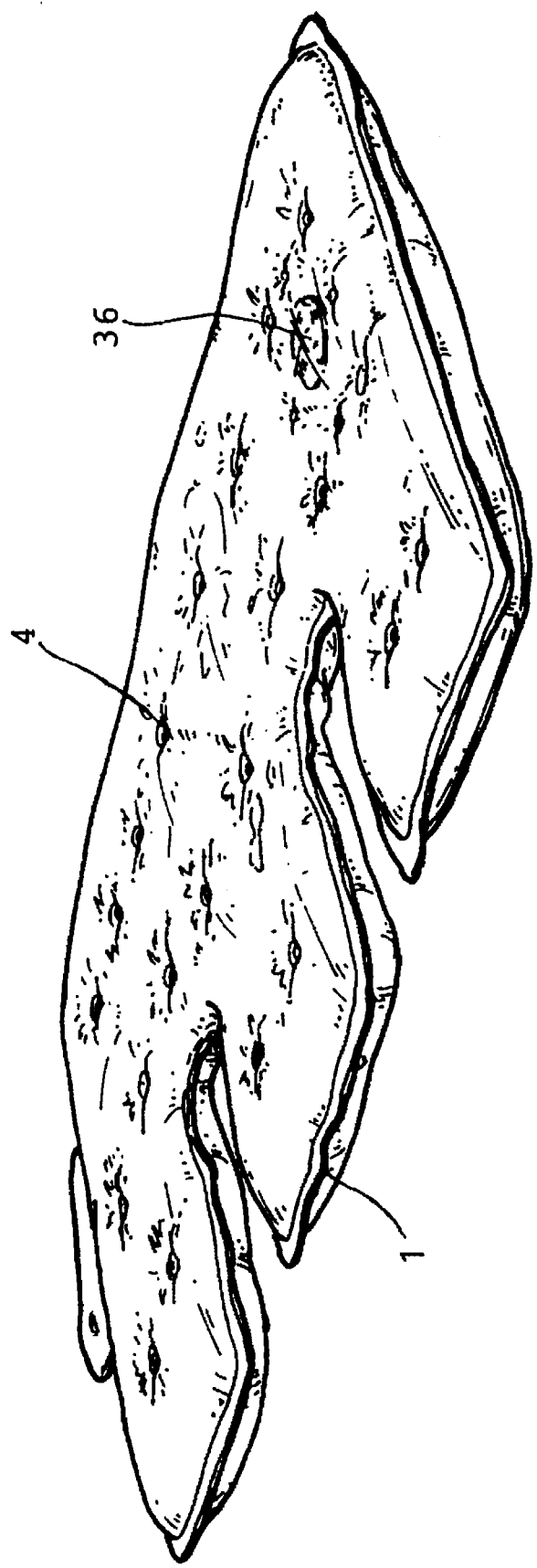
FIG. 3 shows an alternate form of the present invention using a metal spring plate as the activator.

Referring to FIG. 3, the plastic bag 1 has a plurality of internal welds 4 connected between two opposite side walls thereof. The internal welds 4 keep the plastic bag 1 in a flat configuration.

Figure 4:
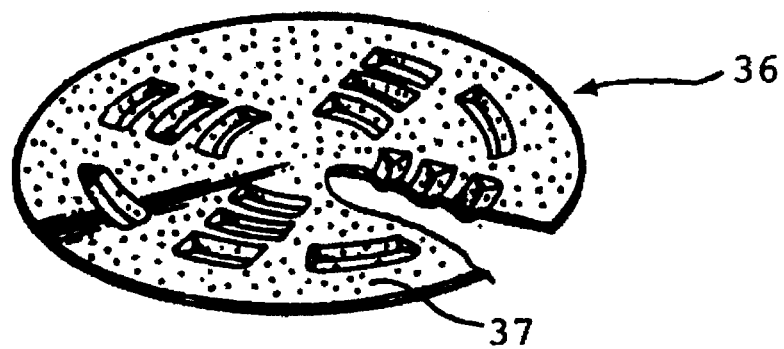
FIG. 4 is perspective view of a metal spring plate according to the present invention.

Referring to FIG. 4 and FIG. 3 again, the aforesaid activator can be a metal plate 36 having a coarse outside wall (frosted) 37. The coarse outside wall 37 of the metal plate 36 reduces the reflection of microwave during the reduction from the liquid phase to the solid phase.

Figure 5:
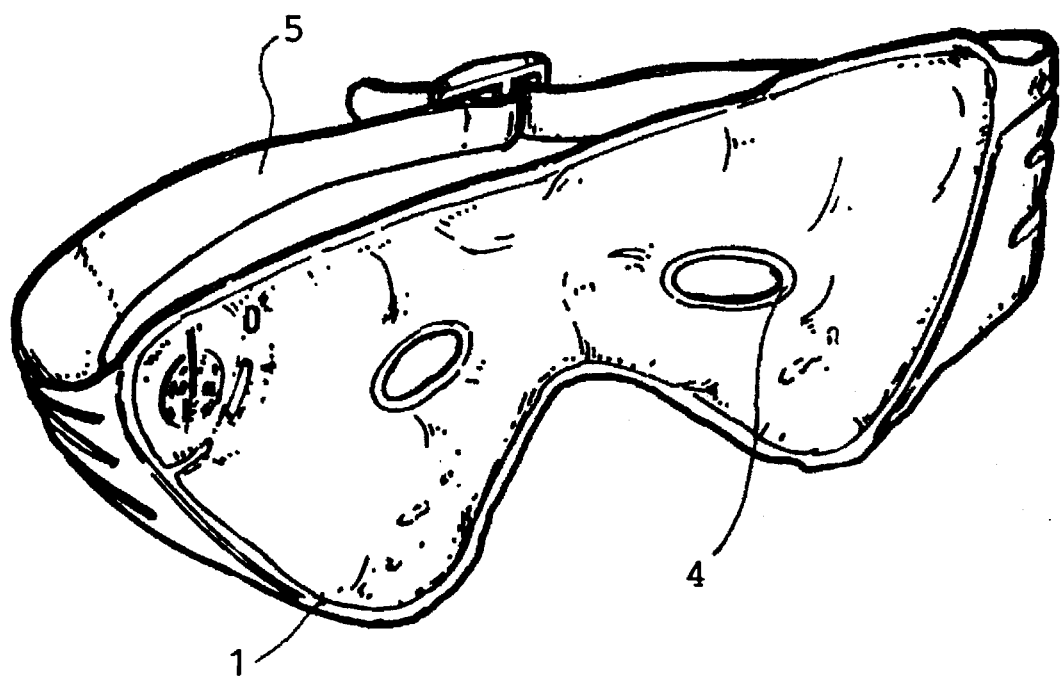
FIG. 5 shows the heat pack made in the form of an eyepiece according to the present invention.

Referring to FIG. 5, the flexible plastic bag 1 can be shaped like an eyepiece, having two internal welds 4 corresponding to the eyes, and a strap 5 for fastening to the head.

Referring to FIG. 4 again, when the metal plate 36 is repeatedly compressed and released, sodium acetate solution 3 is activated to pass from the liquid phase to a crystalline substantially solid phase with the generation of heat and to simultaneously generate heat during the process. By recharging the spent heat pack by the application of microwave energy, crystallized sodium acetate is turned from the substantially solid phase to the liquid phase for a repeat use.

It is to be understood that the drawings are designed for purposes of illustration only, and are not intended as a definition of the limits and scope of the invention disclosed.

I claim:

1. A reusable heat pack regenerated by microwave energy comprising: a flexible water-tight plastic bag having two opposite side walls welded together around a periphery of the heat pack and at least one internal weld connected between said side walls inside the periphery of the heat pack; a saturated sodium acetate solution contained in said plastic bag; and an activator disposed within the bag in contact with said saturated sodium acetate solution, said activator comprising a generally flat metal spring plate having a coarse outside wall to provide a non-reflecting outside surface for microwaves and operated to activate said saturated sodium acetate solution to crystallize.

* * * * *